US00PP36946P2

(12) United States Plant Patent
Schoone

(10) Patent No.: US PP36,946 P2
(45) Date of Patent: Sep. 9, 2025

(54) ***PHALAENOPSIS* PLANT NAMED 'Landmark'**

(50) Latin Name: *Phalaenopsis hybrida*
Varietal Denomination: Landmark

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/171,334

(22) Filed: Apr. 6, 2025

Related U.S. Application Data

(60) Provisional application No. 63/575,712, filed on Apr. 6, 2024.

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Landmark', characterized by its upright plant habit; strong flowering stems; healthy and sturdy leaves; freely flowering habit with typically two inflorescences developing per plant, each inflorescence with numerous flowers; reddish purple-colored flowers with the labella mostly purplish red in color with yellowish white-colored bases; and good postproduction longevity.

2 Drawing Sheets

Figure 1:
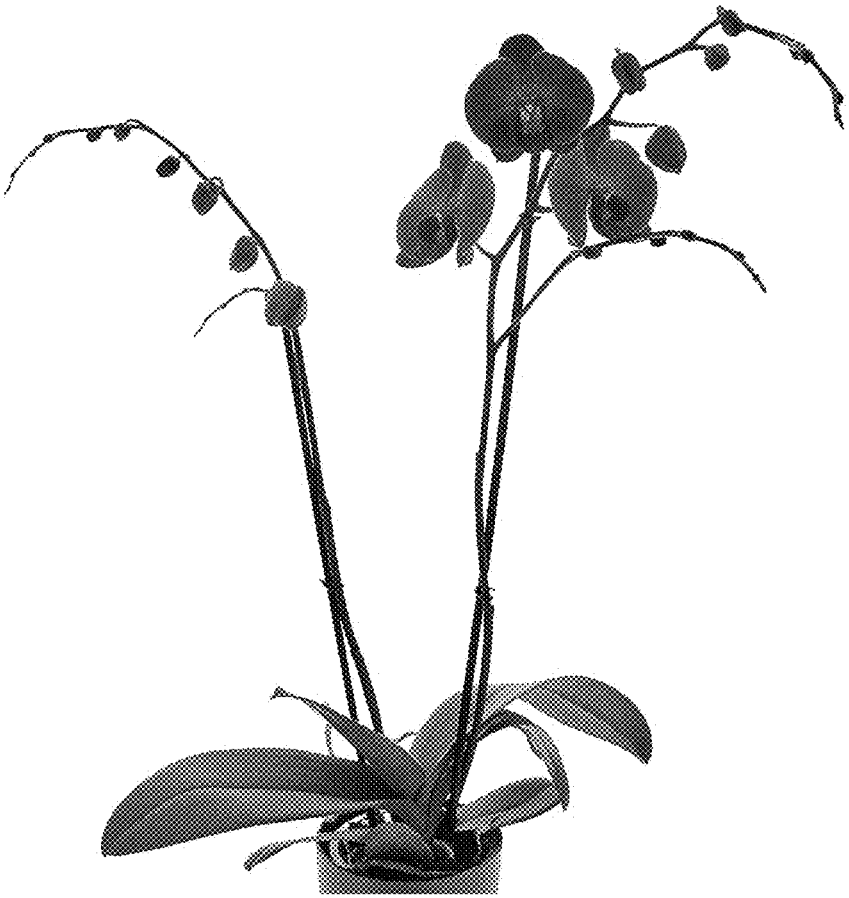

Botanical designation: *Phalaenopsis hybrida.*
Cultivar denomination: 'LANDMARK'.

CROSS-REFERENCED TO CLOSELY-RELATED APPLICATIONS

Title: Varieties of *Phalaenopsis* Plants
Inventor: René Schoone
Filed: Apr. 6, 2024
Serial No. 63/575,712

Inventor and Applicant/Assignee hereby claims the benefit of this provisional U.S. Patent Application.

A European Community Plant Breeder's Rights application for the instant plant was filed by the Applicant/Assignee, Floricultura B.V. of Heemskerk, The Netherlands on Mar. 8, 2024, application number 2024/0611. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Landmark'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in June 2014 in Assendelft, The Netherlands of a proprietary selection of *Phalaenopsis hybrida* with the code designation o.N., not patented, as the female, or seed, parent with *Phalaenopsis hybrida* 'Charleen 2', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in July 2020.

Asexual reproduction of the new *Phalaenopsis* plant by in vitro meristem propagation in a controlled environment in Assendelft, The Netherlands since July 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Landmark'. These characteristics in combination distinguish 'Landmark' as a new and distinct *Phalaenopsis* plant:

1. Upright plant habit.
2. Strong flowering stems.
3. Healthy and sturdy leaves.
4. Freely flowering habit with typically two inflorescences developing per plant, each inflorescence with numerous flowers.
5. Reddish purple-colored flowers with the labella mostly purplish red in color with yellowish white-colored bases.
6. Good postproduction longevity.

Plants of the new *Phalaenopsis* can be compared to plants of the female parent selection. Plants of the new *Phalaen-*

*opsis* differ primarily from plants of the female parent selection in labella coloration as the lateral lobes of the labella of plants of the new *Phalaenopsis* are mostly purplish red in color with yellowish white-colored bases whereas the lateral lobes of the labella of plants of the female parent selection are completely dark purplish red in color. In addition, flowers of plants of the female parent selection have a white-colored haze around the column whereas flowers of plants of the new *Phalaenopsis* do not have a white-colored haze around the column.

Plants of the new *Phalaenopsis* can be compared to plants of the male parent, 'Charleen 2'. Plants of the new *Phalaenopsis* differ primarily from plants of 'Charleen 2' in labella shape as the central lobes of the labella of plants of the new *Phalaenopsis* are broader than the central lobes of the labella of plants of 'Charleen 2'. In addition, the lateral lobes of the labella of plants of 'Charleen 2' are spotted whereas the lateral lobes of the labella of the new *Phalaenopsis* are not spotted.

Plants of the new *Phalaenopsis* can be compared to plants of *Phalaenopsis hybrida* 'Joyride', disclosed in U.S. Plant Pat. No. 29,153. In side-by-side comparisons, plants of the new *Phalaenopsis* differ primarily from plants of 'Joyride' in the following characteristics:

1. Flower petals of plants of the new *Phalaenopsis* are free and not imbricate whereas flower petals of plants of 'Joyride' are touching and imbricate.
2. Flower petals and sepals of plants of the new *Phalaenopsis* have distinct venation whereas flower petals of plants of 'Joyride' do not have distinct venation.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Landmark' grown in a container.

Figure 2:
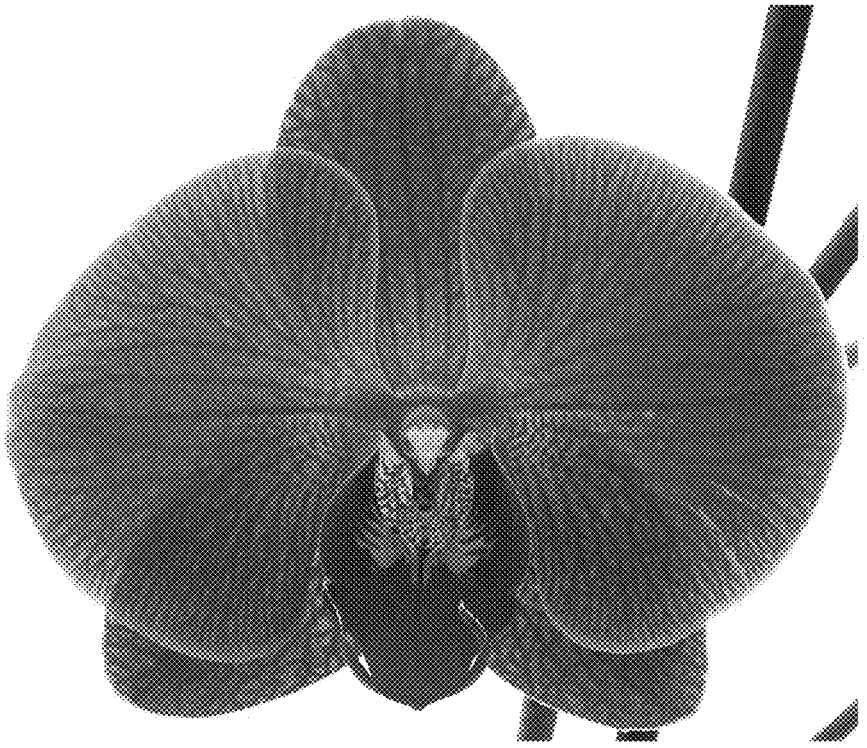

The photograph on the second sheet (FIG. 2) is a close-up view of a typical flower of 'Landmark'.

DETAILED BOTANICAL DESCRIPTION

The aforementioned photographs and following observations and measurements describe plants grown during the late summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Landmark'.

Parentage:

*Female, or seed, parent*.—Proprietary selection of *Phalaenopsis hybrida* with the code designation o.N., not patented.

*Male, or pollen, parent*.—*Phalaenopsis hybrida* 'Charleen 2', not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane*.—About 14 cm.

*Plant height, substrate level to top of floral plane*.—About 54 cm.

*Plant diameter or spread*.—About 44.9 cm.

Leaf description:

*Arrangement and quantity*.—Distichous, simple; sessile; about six to seven fully-developed leaves per plant.

*Length*.—About 22.8 cm.

*Width*.—About 8.1 cm.

*Aspect*.—Semi-erect and outwardly arching.

*Shape*.—Obovate-oblong; slightly carinate.

*Apex*.—Broadly unequal and broadly acute.

*Base*.—Sheathing. Sheath length: About 2 cm. Sheath width: About 1.3 cm. Sheath color, upper and lower surfaces: Close to 143A flushed with close to 143C.

*Margin*.—Entire.

*Texture and luster, upper surface*.—Smooth, glabrous; slightly glossy.

*Texture and luster, lower surface*.—Smooth, glabrous; moderately glossy.

*Venation pattern*.—Camptodromous.

*Color*.—Developing leaves, upper surface: Close to a blend of NN137A and 147A; narrow marginal edges, close to N199A. Developing leaves, lower surface: Close to 146B finely dotted and slightly tinged with close to N186C; marginal edges, close to a blend of N186C and N200A. Fully expanded leaves, upper surface: Close to NN137A; narrow marginal edges, close to 137B; venation, close to a blend of 147A and N189A. Fully expanded leaves, lower surface: Close to 146B; marginal edges, close to N200A; venation, close to N187A.

Inflorescence description:

*Appearance and flowering habit*.—Showy zygomorphic flowers arranged on axillary simple or branched racemes; typically two inflorescences develop per plant; each inflorescence with about 14 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 34.6 cm.

*Inflorescence width*.—About 18.5 cm.

*Flower buds*.—Height: About 2.1 cm. Diameter: About 1.4 cm by 1.6 cm. Shape: Broadly ovate. Color: Close to a blend of N77B and 186A; at the base, tinged with close to 196A; venation, close to N78A.

*Flower size*.—About 8 cm (vertical) by 9.9 cm (horizontal).

*Flower depth*.—About 2.6 cm.

*Petals, quantity and arrangement*.—Three, two lateral petals and one center petal transformed into a labellum.

*Lateral petals*.—Length: About 4.7 cm. Width: About 6.1 cm. Shape: Broadly reniform; not fused. Apex: Obtuse to rounded; occasionally, shallowly retuse. Margin: Entire. Texture and luster, upper surface: Smooth, glabrous; velvety; matte. Texture and luster, lower surface: Smooth, glabrous; moderately velvety; matte. Color: When opening, upper surface: Close to a blend of N78A and NN78A; fading towards the margins and apex to close to N78A; towards the base, close to 77B with radial stripes, close to a blend of 76D and N155A; at the base, close to NN78A; venation, close to a blend of N78A and NN78A; narrow marginal edges, close to 76C. When opening, lower surface: Close to N78B and fading towards the center to close to 76A and N78D; venation, close to N78A. Fully opened, upper surface: Close to a blend of N78A and NN78A; fading towards the margins and apex to close to a blend of N78B and NN78B; towards the base, close to N78C with radial stripes, close to N78D; at the base, close to NN78A; venation, close to a blend of N78A and NN78A; narrow marginal edges, close to 76C; colors do not change with subsequent development. Fully opened, lower surface: Close to N78B and fading towards the center to close to N78C and N78D; venation, close to a blend of N78A and NN78A; color s do not change with subsequent development.

*Labella*.—Appearance: Three-parted with two lateral lobes and a central lobe. Length, lateral lobes: About 1.9 cm. Width, lateral lobes: About 1.8 cm. Length, central lobe: About 2.3 cm. Width, central lobe: About 1 cm to 2.3 cm. Shape, lateral lobes: Obovate; slightly curved. Shape, central lobe: Deltoid-ovate with an elongated apex. Apex, lateral lobes: Obtuse. Apex, central lobe: Cleft with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5 mm in length, about 6 mm in width and about 6 mm in height. Color, lateral lobes: When opening, upper surface: Close to 187C; towards the apex, close to 72A and 72B; at the base, blotched and striped with close to NN155B. When opening, lower surface: Close to N186D; towards the apex, close to N78A; at the base, blotched and striped with close to N155A. Fully opened, upper surface: Close to 187C; towards the apex, close to 72A and 72B; at the base, blotched and striped with close to 158C. Fully opened, lower surface: Close to N186D; towards the apex, close to N78A; at the base, blotched and striped with close to N155A. Color, central lobe: When opening and fully opened, upper surface: Close to 71A fading to close to a blend of 71A and N186D; faint blotch towards the margins, close to 162B; at the base, close to a blend of N155A and N155B with radial stripes, close to 185A; cirrhose apices, close to 71A fading to close to a blend of 71A and N186D. When opening and fully opened, lower surface: Close to N78A and NN78A; at the broadest part, close to 187C; small apical blotch, close to 75A; faint apical blotch towards the margins, close to 162B; at the base, close to N155A with radial stripes, close to 71A; cirrhose apices, close to 72A. Color, callosities: When developing: Close to NN155B sparsely covered with fine dots, close to 183B; towards the apex, close to 13C densely dotted and blotched with close to 183B. Fully developed: Close to 4D sparsely covered with fine dots, close to 183B; towards the apex, close to 13B densely dotted and blotched with close to 183B.

*Sepals*.—Quantity and arrangement: Three, one upper dorsal sepal and two lower lateral sepals. Length, dorsal sepal: About 4.7 cm. Width, dorsal sepal: About 3.4 cm. Length, lateral sepals: About 4.8 cm. Width, lateral sepals: About 3.2 cm. Shape, dorsal sepal: Broadly elliptic. Shape, lateral sepals: Ovate. Apex, dorsal sepal: Minutely retuse. Apex, lateral sepals: Narrowly obtuse. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to N78A; towards the base, close to N78B; narrow marginal edges, close to 76B; venation, close to a blend of NN78A and N79C. When opening, lower surface: Close to 70A; at the apex, close to N78B; marginal edges, close to N78B; venation, close to N78A. Fully opened, upper surface: Close to NN78A; towards the apex and base, close to N78A; narrow marginal edges, close to 76B; venation, close to a blend of NN78A and N79C. Fully opened, lower surface: Close to 70A; at the apex, close to N78B; marginal edges, close to N78B; venation, close to a blend of N78A and NN78A. Color, lateral sepals: When opening, upper surface: Close to N78B; towards the base, close to a blend of 77D and N155A; at the base, blotch, close to 159C; venation, close to NN78A, N79C and a blend of NN78A and N79C. When opening, lower surface: Close to N77B and a blend of N77B and N78B; proximally, tinged with close to 182C; main vein, close to 71A and lateral venation, close to N78A. Fully opened, upper surface: Close to N78B; towards the base, close to 77C and 77D; at the base, blotch, close to 155C; venation, close to NN78A and a blend of NN78A and N79C. Fully opened, lower surface: Close to N78B; towards the margins and apex, close to a blend of N78A and N78B; proximally, tinged with close to 182C; main vein, close to 72A and lateral venation, close to N78A.

*Peduncles*.—Length: About 67.3 cm. Diameter: About 6 mm. Strength: Strong. Aspect: Upright to outwardly arching. Texture and luster: Smooth, glabrous; matte. Color: Close to a blend of N198A and N200A densely covered with fine dots, close to 147C.

*Pedicels*.—Length: About 4.1 cm. Diameter: About 3.5 mm. Strength: Moderately strong. Aspect: About 70° from peduncle axis. Texture and luster: Smooth, glabrous; matte. Color: Close to 182B tinged with close to 197B; distal end, close to 75B to 75D; proximal end, close to a blend of N189A and 203B.

*Reproductive organs*.—Androecium: Column length: About 1 cm. Column width: About 6 mm. Column color: Close to N78A and N78B; distally, close to N78D; at the base, close to NN78A. Pollinia quantity: Two. Pollinia diameter (per two pollinia): About 2.25 mm. Pollinia color: Close to 23A. Gynoecium: Stigma length: About 3.5 mm. Stigma width: About 4 mm. Stigma shape: Reniform. Stigma color: Close to N155A. Ovary length: About 1 cm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Landmark' as herein illustrated and described.

* * * * *